Figure 1:
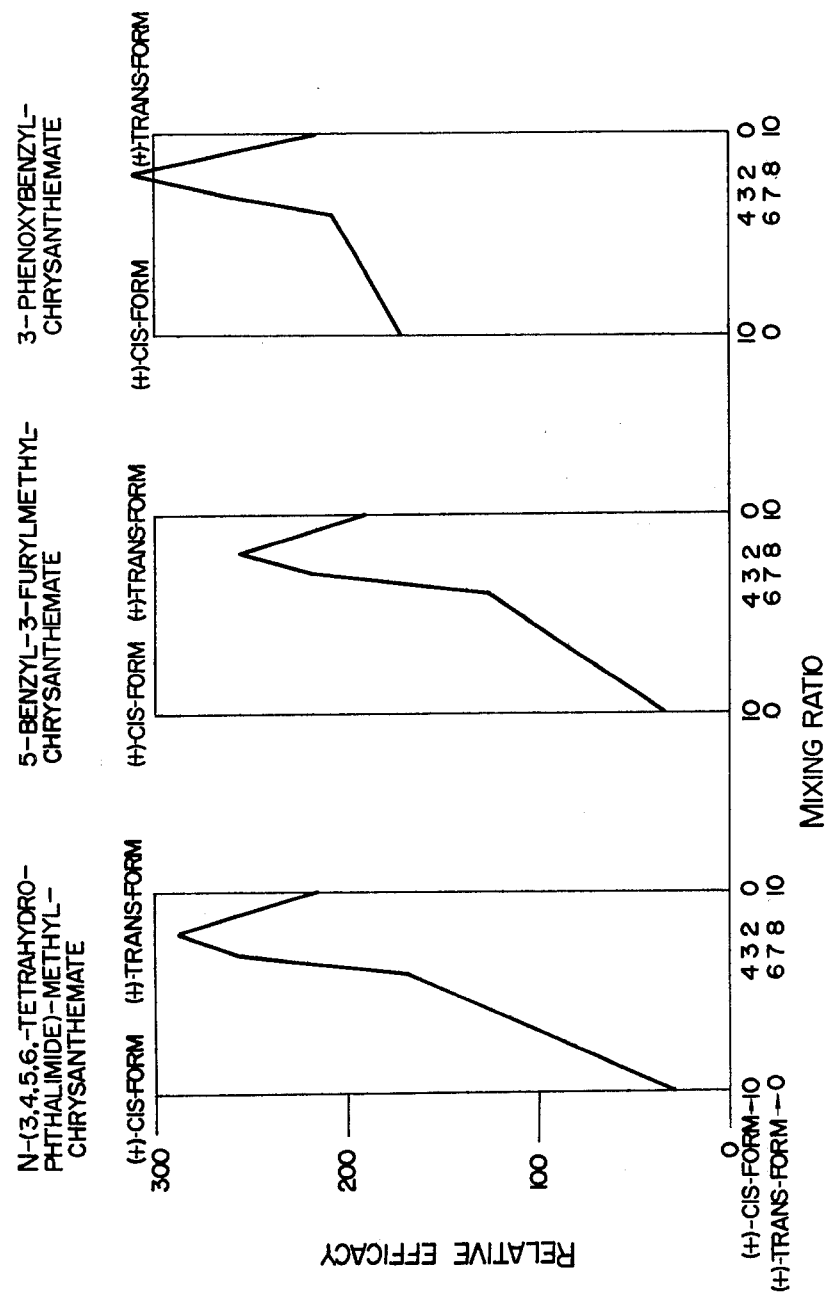

United States Patent
Okuno et al.

[11] 3,934,023
[45] Jan. 20, 1976

[54] INSECTICIDAL D-CIS, TRANS-CHRYSANTHEMATES

[75] Inventors: Yoshitoshi Okuno, Toyonaka; Akira Toyoura; Akio Higo, both of Nishinomiya, all of Japan

[73] Assignee: Sumitomo Chemical Company, Limited, Osaka, Japan

[22] Filed: Sept. 26, 1973

[21] Appl. No.: 401,034

[30] Foreign Application Priority Data
Sept. 29, 1972 Japan............... 47-98458

[52] U.S. Cl. .............. 424/274; 424/285; 424/306
[51] Int. Cl.[2]... A01N 9/22; A01N 9/24; A01N 9/28
[58] Field of Search.................... 424/285, 274, 306

[56] References Cited
UNITED STATES PATENTS

| | | | |
|---|---|---|---|
| 3,268,551 | 8/1966 | Kuramoto et al. | 424/306 |
| 3,702,333 | 11/1972 | Nakanishi et al. | 424/285 |
| 3,714,153 | 1/1973 | Martel et al. | 424/285 |
| 3,723,615 | 3/1973 | Okuno | 424/285 |
| 3,766,218 | 10/1973 | Veda et al. | 424/285 |
| 3,767,806 | 10/1973 | Rauch | 424/306 |

*Primary Examiner*—V. D. Turner
*Attorney, Agent, or Firm*—Stevens, Davis, Miller & Mosher

[57] ABSTRACT

An insecticidal composition containing as an active ingredient an insecticidally effective amount of 10 to 30 % by weight of (+)-cis- and 70 to 90 % by weight of (+)-trans-chrysanthemate of the formula

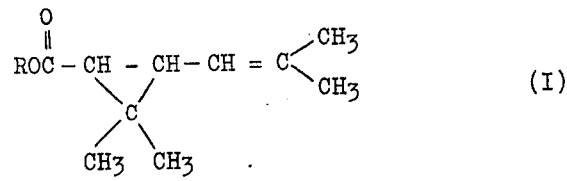

(I)

wherein R is

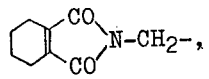

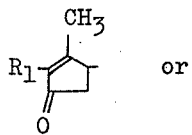

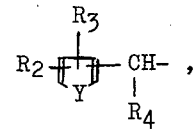

in which $R_1$ is an allyl or propargyl group, $R_2$ is a propargyl, benzyl or phenoxy group, $R_3$ is a hydrogen atom or a methyl group, $R_4$ is a hydrogen atom or an ethynyl group and Y is an oxygen atom or —CH=CH— group; and An insecticidal composition containing as an active ingredient an insecticidally effective amount of (a) at least one of above-mentioned (+)-cis,trans-chrysanthemates having said cis to trans ratio and (b) at least one of chrysanthemates prepared from a chrysanthemic acid having a cis to trans ratio different from that of the (+)-cis,trans-chrysanthemic acid moiety of the above formula (I) and an alcohol moiety of the above formula (I) having a structure different from that of the alcohol moiety of the (+)-cis,trans-chrysanthemates of above (a).

The (+)-cis,trans-chrysanthemates having said cis to trans ratio show an excellent insecticidal effect as well as a strong synergistic effect on the chrysanthemates of above (b).

19 Claims, 2 Drawing Figures

INSECTICIDAL D-CIS, TRANS-CHRYSANTHEMATES

The present invention relates to a (+)-cis, trans-chrysanthemate, an insecticidal composition containing the following first component or the first and second components as an active ingredient, and to the preparation thereof. The first component consists of one or more of a (+)-cis, trans-chrysanthemate of the formula,

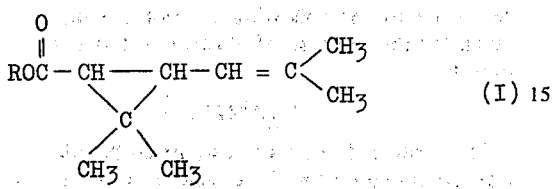

wherein R is

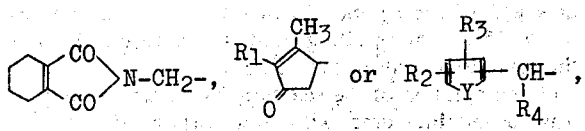

in which $R_1$ is an allyl or propargyl group, $R_2$ is a propargyl, benzyl or phenoxy group, $R_3$ is a hydrogen atom or a methyl group, $R_4$ is a hydrogen atom or an ethynyl group and Y is an oxygen atom or —CH=CH— group, which is prepared by esterifying a new chrysanthemic acid obtained according to the inventors' new method and having isomer ratio different from that of a conventional chrysanthemic acid, namely, (+)-cis, trans-chrysanthemic acid containing 10 to 30 % by weight of (+)-cis-chrysanthemic acid, 70 to 90 % by weight of (+)-trans-chrysanthemic acid and no (—)-cis, trans-chrysanthemic acid, with an alcohol of the formula (II) as shown hereinafter. The second component consists of one or more of said chrysanthemates and one or more of chrysanthemates whose acid moiety has an isomer ratio different from that of said chrysanthemates and whose alcohol moiety is an alcohol represented by the formula (II) and is different from that of said chrysanthemates.

More particularly, one object of the present invention is to provide (+)-cis, trans-chrysanthemic acid esters prepared by esterifying (+)-cis, trans-chrysanthemic acid of a new isomer ratio with alcohols of the formula,

R — OH     (II)

wherein R is the same meanings as defined above. Another object of the present invention is to provide an insecticidal composition for sanitation, household horticulture, agriculture, and woods and forests by utilizing an insecticidal activity of said esters or a synergistic action obtained by mixing at least one or more of said esters and one or more of esters whose acid moiety has an isomer ratio different from that of said esters and whose alcohol moiety is an alcohol represented by the formula (II) and is different from that of said esters. Said (+)-cis, trans-chrysanthemates contained in the present compositions may, of course, be prepared by other methods, in addition to the method of the present invention, or by mixing (+)-cis- and (+)-trans-chrysanthemates which have been prepared independently.

Various types of chrysanthemates whose acid moiety is an isomer mixture of chrysanthemic acid have been used as insecticides, and the acid which has been prepared by the conventional industrial methods most readily and cheaply, and used widely as insecticides is (±)-cis, trans-chrysanthemic acid.

On the other hand, since (+)-trans-chrysanthemic acid, among those acid moieties, is known to give its esters of the highest insecticidal activity, insecticides of (+)-trans-chrysanthemic acid type is also about to be used in practice, using a method including an optical resolution of racemate which is industrially uneconomical.

The present inventors made a study of a synergistic action between the isomers on the insecticidal activity by mixing esters of each isomer, and found a surprising fact that mixing of a (+)-trans-form having the highest insecticidal activity among the isomers and a (+)-cis-form within a range between 7 : 3 and 9 : 1, respectively, of a (+)-trans-form to (+)-cis-form ratio, most preferably 8 : 2, has a remarkable synergistic effect. When used practically, the compounds of the present invention were formulated into a composition containing 0.05 to 90 % by weight of active ingredient. In addition, the inventors found that contamination with (—)-isomers such as a (—)-trans- or (—)-cis-form gives an adverse effect on an insecticidal activity rather than giving no effect on its activity. As mentioned hereinbefore, the removal of the (—)-isomers from the (+)-isomers contaminated with (—)-isomers has a large singnificance in the biological activity, which is a new knowledge first discovered by the inventors. Furthermore, it was found that a mixed preparation described above containing the (+)-isomers and other chrysanthemates also shows a remarkable synergistic effect.

The inventors, as a result of a study on the preparation of (+)-cis,trans-chrysanthemic acid, found the following new method.

That is, when (±)-cis,trans-chrysanthemic acid having a particular isomer ratio is converted to a particular amine salt thereof, and then subjected to an optical resolution in a polar solvent, both a cis- and trans-form in a mixed chrysanthemic acid obtained from the crystallized salt are (+)-type one, namely dextrorotatory (in chloroform or ethanol only), and in addition, a ratio of cis-form to trans-form is kept unchanged substantially before and after the optical resolution, under a suitable condition. Furthermore, it was unexpectedly found that, when the crystallization is carried out under stirring, both the (+)-cis-and the (+)-trans-type acid have a higher optical purity than that of a (+)-trans-form obtained from a (±)-trans-form alone under the same optical resolution. Thus, according to the present invention, the industrial optical resolution of chrysanthemic acid became easier than that of (±)-trans-acid with said amine, and the optical resolution of a cis,-trans-mixed chrysanthemic acid became possible for the first time.

The optically active organic bases used in the present invention include (+)-α-phenyl-β-p-tolylethylamine, (+)-α-p-tolyl-β-phenylethylamine, and (+)-α-phenyl-β-phenyl-ethylamine.

The effect of optical resolution above mentioned begins to appear when a (±)-cis-chrysanthemic acid content of a (±)-mixed-chrysanthemic acid reaches 3

% by weight, and is increased with an increase of its content. In general, the optical resolution can be carried out at a range of above 3 % by weight of the content, and it is particularly advantageous at a range from 10 to 30 % by weight in suitable solvents such as methanol, ethanol, propanol, acetone, methyl ethyl ketone and a mixture thereof with water.

Thus, according to the present invention, it became possible that the resolution of optical isomers was carried out more readily and in a higher yield than obtaining a (+)-trans-chrysanthemic acid and a (+)-cis, trans-chrysanthemic acid was obtained advantageously and economically in industry.

The object of the present invention is to prepare (+)-cis, trans-chrysanthemate by reacting (+)- cis, trans-chrysanthemic acid of a new isomer ratio thus obtained, or reactive derivatives thereof with alcohols of the formula (I), and to provide an insecticidal composition containing the said chrysanthemates. It is of course that said (+)-cis, trans-chrysanthemic acids may be prepared by any other method.

Of the (+)-cis,trans-chrysanthemates according to the present invention, the esters whose cis-form to trans-form ratio is 2 : 8 are exemplified as follows, but not limitative thereto.

Compound (1); N-(3,4,5,6-tetrahydrophthalimide)-methyl-(+)-cis,trans-chrysanthemate Compound (2); (±)-2-allyl-3-methylcyclopent-2-ene-1-one-4-yl-(+)-cis,trans-chrysanthemate Compound (3); (±)-2-propargyl-3-methylcyclopent-2-ene-1-one-4-(+)-cis,trans-chrysanthemate Compound (4); (+)-2-allyl-3-methylcyclopent-2-ene-1-one-4-yl-(+)-cis,trans-chrysanthemate Compound (5); (+)-2-propargyl-3-methylcyclopent-2-ene-1-one-4-yl-(+)-cis,trans-chrysanthemate Compound (6); 5-benzyl-3-furylmethyl-(+)-cis,-trans-chrysanthemate Compound (7); 5-phenoxy-furfuryl-(+)-cis,trans-chrysanthemate Compound (8); 5-propargylfurfuryl-(+)-cis,trans-chrysanthemate Compound (9); 5-propargyl-2-methyl-3-furylmethyl-(+)-cis,trans-chrysanthemate Compound (10); (±)-5-propargyl-α-ethynyl-furfuryl-(+)-cis,trans-chrysanthemate Compound (11); 3-benzylbenzyl-(+)-cis,trans-chrysanthemate Compound (12); 3-phenoxybenzyl-(+)-cis,trans-chrysanthemate Mixtures consisting of one or more of the new (+)-cis,trans-chrysanthemates, or mixtures consisting of one or more of said chrysanthemates and one or more of esters whose acid moiety has a different isomer ratio from that of said chrysanthemates and whose alcohol moiety is an alcohol represented by the formula (I) and is different from that of said chrysanthemates, give a remarkable synergistic effect. And the insecticidal compositions of the present invention containing the mixtures as an active ingredient are widely used as a very valuable insecticide, owing to their immediate effect, strong insecticidal activity and low toxicity to mammals, in controlling not only insects injurious to sanitation, but also insects injurious to agriculture, household horticulture, stored cereals, and woods and forests.

The present compositions can be used without problems, particularly owing to their low toxicity to mammals, for agricultural crops before harvest, greenhouse cultivation, household horticulture and food-packaging. The mixed preparations having a synergistic effect show a high insectical activity when they contain 0.2 to 90 % by weight of two or more active ingredients, one of which is a (+)-cis,trans-chrysanthemate having above mentioned ratio, and contain the (+)-cis,trans-chrysanthemate and other chrysanthemates in the proportion of 10 : 2 – 50, preferably 10 : 2.5 – 40 respectively.

The preparation of the (+)-cis,trans-chrysanthemic acids of the present invention will be illustrated with reference to the following examples, which are only given for the purpose of illustration but not limitative thereto.

EXAMPLE 1

35.2 Grams of (+)-cis,trans-chrysanthemic acid chloride containing 18.8 % by weight of (+)-cis-chrysanthemic acid chloride were dissolved in 90 ml of toluene. The solution was added to a mixture of 33.2 g of N-(3,4,5,6-tetrahydrophthalimide)-methylalcohol, 21.7 g of pyridine and 180 ml of toluene over 45 minutes while keeping the reaction temperature at from 30° to 35°C. The resulting solution was further kept at the same temperature for 5 hours.

On completion of the reaction, the reaction mixture was washed three times with three portions of 150 ml of a 10 % hydrochloric acid, and then with 300 ml of an 1 % aqueous sodium hydroxide solution, 300 ml of water and 300 ml of a saturated sodium chloride solution in this order. The toluene layer thus obtained was dried over anhydrous magnesium sulfate, and 33 g of alumina and 16 g of silica gel were added to the solution, which was then stirred for 30 minutes at room temperature. After removing alumina and silica gel by filtration, the solution was concentrated under a reduced pressure to give 56.7 g of N-(3,4,5,6-tetra-hydrophthalimide)-methyl-(+)-cis,trans-chrysanthemate as an oil.

$[\alpha]_D^{23} = -15.13°$ [CHCl$_3$]C = 4.15 %; $n_D^{28} = 1.5182$

EXAMPLE 2

29.2 Grams of (+)-cis,trans-chrysanthemic acid chloride containing 17.7 % by weight of (+)-cis-chrysanthemic acid chloride were dissolved in 30 ml of toluene. The solution was added to a mixture of 25.0 g of (±)-2-allyl-3-methylcyclopent-2-ene-1-one-4-ol, 18.6 g of pyridine and 40 ml of toluene over 30 minutes while keeping the reaction temperature at from 40° to 50°C. The solution was further kept at the same temperature for 4 hours.

Thereafter, the reaction solution was treated in the same manner as described in Example 1 to give 45.8 g of (±)-2-allyl-3-methylcyclopent-2-ene-1-one-4-yl-(+)-cis,trans-chrysanthemate as an oil.

$[\alpha]_D^{23} = +3.12°$ [CHCl$_3$]C = 7.6 %; $n_D^{28} = 1.5050$

EXAMPLE 3

61.7 Grams of (+)-cis,trans-chrysanthemic acid chloride containing 18.7 % by weight of (+)-cis-chrysanthemic acid chloride were dissolved in 170 ml of toluene. The solution was added to a mixture of 58.1 g of 5-benzyl-3-furylmethylalcohol, 36.6 g of pyridine and 185 ml of toluene over 2 hours while keeping the reaction temperature at from 25° to 30°C. The solution was further kept at the same temperature for 5 hours. Thereafter, the reaction solution was treated in the same manner as described in Example 1 to give 105.4 g of 5-benzyl-3-furylmethyl-(+)-cis,trans-chrysanthemate as an oily matter. $[\alpha]_D^{23} = -2.45°$ [CHCl$_3$]C = 3.3 %; $n_D^{28}$ = 1.5290

EXAMPLE 4

A solution of 56.8 g of 5-propargylfuryl alcohol dissolved in 157.8 g of toluene was cooled to below 10°C, and 63.3 g of triethylamine were added thereto. The mixture was cooled again to below 10°C, and a solution of 81.8 g of (+)-cis,trans-chrysanthemic acid chloride containing 19.0 % by weight of (+)-cis-chrysanthemic acid chloride in 186.8 g of toluene was added thereto at a temperature of below 40°C. The mixture was further maintained at from 35° to 40°C for 3 hours. Thereafter, the reaction solution was treated in the same manner as described in Example 1 to give 105 g of 5-propargyl-furfuryl-(+)-cis,trans-chrysanthemate as an oil.
$[\alpha]_D^{24} = -17.54°$ [CHCl$_3$]C = 20.5 %; $n_D^{21.5}$ = 1.5076

EXAMPLE 5

A mixture of 25.7 g of (+)-cis,trans-chrysanthemic acid chloride containing 15.2 % of (+)-cis-chrysanthemic acid chloride, and 80 ml of toluene was cooled to from −20° to −25°C, and then 15.9 g of triethylamine were added thereto at the same temperature. After stirring for 15 minutes at the same temperature, a solution of 21.0 g of 5-propargyl-α-ethynylfurfurylalcohol in 20 ml of toluene was added dropwise thereto.

After addition, the mixture was gradually returned to room temperature, and maintained at from 20° to 25°C while stirring.

Thereafter, the solution was treated in the same way as described in Example 1 to give 40.9 g of 5-propargyl-α-ethynylfurfuryl-(+)-cis,trans-chrysanthemate as an oil. TI $[\alpha]_D^{24} = -7.57°$ [CHCl$_3$]C = 5.81 %; $n_D^{28}$ = 1.5098

EXAMPLE 6

85.0 Grams of (+)-cis,trans-chrysanthemic acid chloride containing 16.0 % by weight of (+)-cis-chrysanthemic acid chloride were dissolved in 270 ml of toluene. The solution was added to a mixture of 86.75 g of 3-phenoxy-benzylalcohol, 51.4 g of pyridine and 270 ml of toluene over 1 hour while keeping the reaction temperature at from 20° to 30°C. The solution was further maintained at the same temperature for 4 hours. Thereafter, the reaction solution was treated in the same way as described in Example 1 to give 148.5 g of 3-phenoxybenzyl-(+)-cis,trans-chrysanthemate as an oil.
$[\alpha]_D^{27} = -6.43°$ [CHCl$_3$]C = 9.672 %; $n_D^{28}$ = 1.5048

EXAMPLE 7

18.7 Grams of (+)-cis,trans-chrysanthemic acid chloride containing 19.0 % by weight of (+)-cis-chrysanthemic acid chloride were dissolved in 20 ml of toluene. the solution was added to a mixture of 16.0 g of (+)-2-allyl-3-methylcyclopent-2-ene-1-one-4-ol, 11.9 g of pyridine and 30 ml of toluene over 30 minutes while maintaining the reaction temperature at from 40° to 50°C. The solution was further maintained at the same temperature for 4 hours. Thereafter the reaction solution was treated in the same manner as described in Example 1 to give 29.4 g of (+)-2-allyl-3-methylcyclopent-2-ene-1-one-4-yl-(+)-cis,trans-chrysanthemate as an oily matter.
$[\alpha]_D^{22} = -23.01°$ [n-Hexane]C = 1.069 %; $n_D^{28}$ = 1.5098

EXAMPLE 8

11 Grams of (+)-cis,trans-chrysanthemic acid chloride containing 19 % by weight of (+)-cis-chrysanthemic acid chloride were dissolved in 30 ml of toluene. The solution was added to a mixture of 8 g of (±)-2-propargyl-3-methylcyclopent-2-ene-1-one-4-ol, 5.6 g of pyridine and 50 ml of toluene over 1 hour while keeping the reaction temperature at from 20° to 30°C. The solution was further maintained at the same temperature for 6 hours. Thereafter, the reaction solution was treated in the same manner as described in Example 1 to give 6 g of (±)-2-propargyl-3-methylcyclopent-2-ene-1-one-4-yl-(+)-cis,trans-chrysanthemate as an oily matter. $n_D^{22}$ = 1.5199

The present invention will be further illustrated with reference to the following test examples, for the purpose of clarifying the superiority of the present (+)-cis,trans-chrysanthemate type insecticides, and the outstanding synergistic effect of the mixing of two or more of said chrysanthemates, or the mixing of said chrysanthemates and different type chrysanthemates above mentioned.

TEST EXAMPLE 1

In order to investigate the synergistic action between (+)-cis- and (+)-trans-chrysanthemates both of which contain, as an alcohol moiety, N-(3,4,5,6-tetrahydrophthalimide)-methylol, 5-benzyl-3-furylmethylol, 3-phenoxybenzylalcohol, (±)-2-allyl-3-methylcyclopent-2-ene-1-one-4-ol or (+)-2-allyl-3-methylcyclopent-2-ene-1-one-4-ol, the (+)-cis- and the (+)-trans-type esters were individually formulated into their oil sprays as shown in the following Table 1 using a deodorized kerosene. Each 5 ml of the oil sprays formulated was sprayed, using Campbel's turn table apparatus ["Soap and Sanitary Chemicals", Vol. 14, No. 6, 119 (1938)]. A shutter was opened for 20 seconds after spraying, and about 100 house-fly adults (*Musca domestica*) per group were exposed to the descending mist for 10 minutes, and then transferred to an observation cage. In the cage, the flies were fed and allowed to stand for one day at room temperature. Thereafter, the number of killed flies was counted to calculate the mortality.

Figure 2:
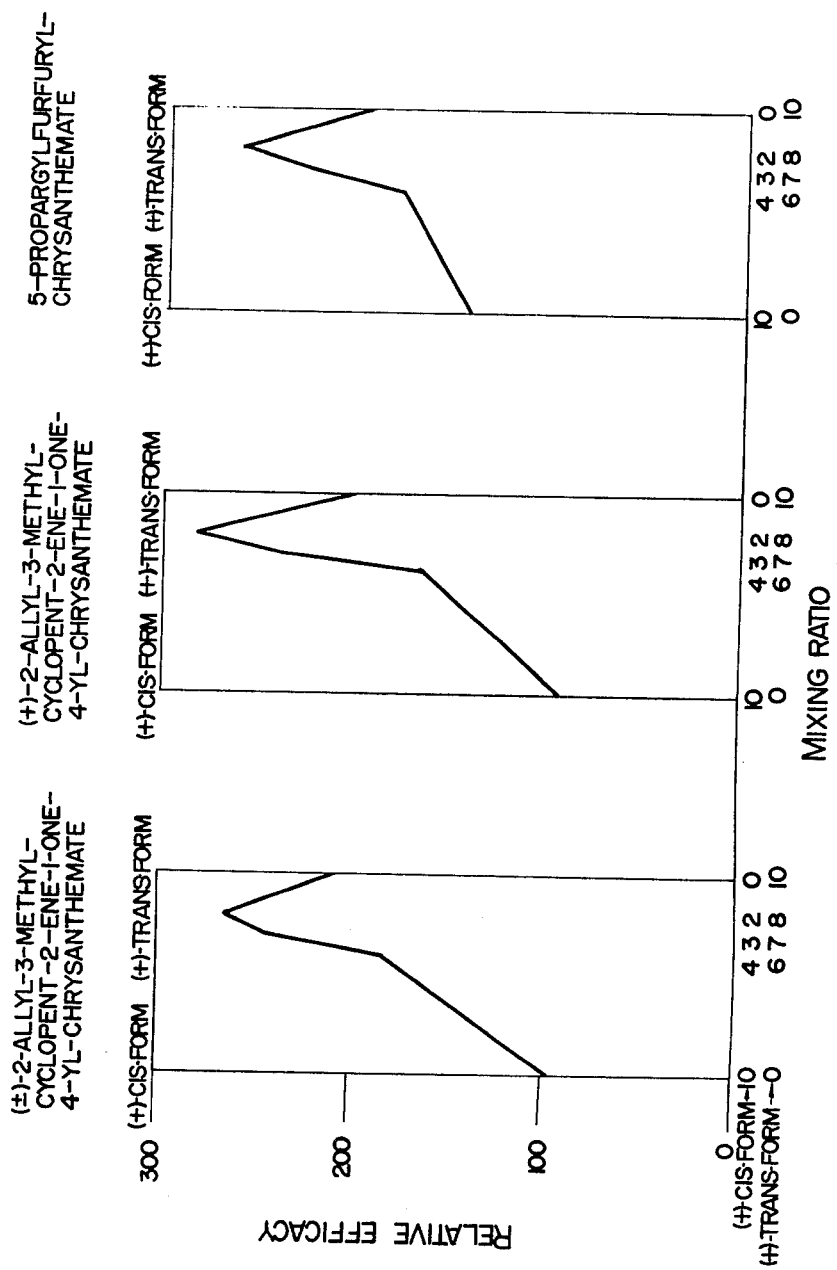

The values of LC$_{50}$ (50 % lethal concentration) are as shown in Table 1 and the attached FIGS. 1 and 2.

From Table 1 and FIGS. 1 and 2, it can clearly be seen that the (±)-trans-chrysanthemate mixed with a small amount of (+)-cis-chrysanthemate shows a higher activity than itself having the highest activity among the esters, and that the synergistic effect is particularly remarkable at a cis-form to trans-form ratio of 2 : 8.

Table 1

| Samples to be tested | LC$_{50}$ (mg/100 ml) | Relative efficacy |
|---|---|---|
| N-(3,4,5,6-tetrahydrophthalimide)-methyl-(±)(1:1)-cis,trans(3:7)-chrysanthemate | 175 | taken as 100 |
| ″  -(+)-trans-chrysanthemate | 80 | 219 |
| ″  -(+)-cis-chrysanthemate | 627 | 28 |

Table 1-continued

| Samples to be tested | | $LC_{50}$ (mg/100 ml) | Relative efficacy |
|---|---|---|---|
| " | -(+)-cis,trans(4:6)-chrysanthemate | 104 | 168 |
| " | -(+)-cis,trans(3:7)-chrysanthemate | 68 | 258 |
| " | -(+)-cis,trans(2:8)-chrysanthemate | 61 | 287 |
| 5-benzyl-3-furylmethyl-(±)(1:1)-cis,trans(3:7)-chrysanthemate | | 19 | taken as 100 |
| " | -(+)-trans-chrysanthemate | 10 | 190 |
| " | -(+)-cis-chrysanthemate | 54 | 35 |
| " | -(+)-cis,trans(4:6)-chrysanthemate | 15 | 127 |
| " | -(+)-cis,trans(3:7)-chrysanthemate | 8.7 | 218 |
| " | -(+)-cis,trans(2:8)-chrysanthemate | 7.4 | 257 |
| 3-phenoxybenzyl-(±)(1:1)-cis,trans(3:7)-chrysanthemate | | 50 | taken as 100 |
| " | -(+)-trans-chrysanthemate | 23 | 217 |
| " | -(+)-cis-chrysanthemate | 29 | 172 |
| " | -(+)-cis,trans(4:6)-chrysanthemate | 24 | 208 |
| " | -(+)-cis,trans(3:7)-chrysanthemate | 19 | 263 |
| " | -(+)-cis,trans(2:8)-chrysanthemate | 16 | 312 |
| (±)-2-allyl-3-methylcyclopent-2-ene-1-one-4-yl-(±)(1:1)-cis,trans(3:7)-chrysanthemate | | 70 | taken as 100 |
| " | -(+)-trans-chrysanthemate | 82 | 207 |
| " | -(+)-cis-chrysanthemate | 178 | 96 |
| " | -(+)-cis,trans(4:6)-chrysanthemate | 93 | 183 |
| " | -(+)-cis,trans(3:7)-chrysanthemate | 70 | 243 |
| " | -(+)-cis,trans(2:8)-chrysanthemate | 64 | 266 |
| (+)-2-allyl-3-methylcyclopent-2-ene-1-one-4-yl-(±)(1:1)-cis,trans(3:7)-chrysanthemate | | 88 | taken as 100 |
| " | -(+)-trans-chrysanthemate | 43 | 205 |
| " | -(+)-cis-chrysanthemate | 95 | 93 |
| " | -(+)-cis,trans(4:6)-chrysanthemate | 53 | 166 |
| " | -(+)-cis,trans(3:7)-chrysanthemate | 37 | 239 |
| " | -(+)-cis,trans(2:8)-chrysanthemate | 31 | 284 |
| 5-propargyl-furfuryl-(±)(1:1)-cis,trans(3:7)-chrysanthemate | | 97 | taken as 100 |
| " | -(+)-trans-chrysanthemate | 49 | 198 |
| " | -(+)-cis-chrysanthemate | 67 | 145 |
| " | -(+)-cis,trans(4:6)-chrysanthemate | 54 | 180 |
| " | -(+)-cis,trans(3:7)-chrysanthemate | 43 | 226 |
| " | -(+)-cis,trans(2:8)-chrysanthemate | 37 | 262 |

TEST EXAMPLE 2

In order to investigate the synergistic action between (+)-cis,trans (for example 2:8)-chrysanthemates themselves, and between said chrysanthemates and the different type chrysanthemates according to the present invention, the two chrysanthemates were formulated into aerosols shown in the following Table 2 according to Preparation 10 described hereinafter. Then the insecticidal activity of the aerosols on house-fly adults (*Musca domestica*) was tested by the aerosol test method using a (6 ft)$^3$ Peet Grady's chamber [the method disclosed in "Soap and Chemical Specialities, Blue Book" (1965)]. The results are as shown in Tables 2 and 3.

A concentration of 0.1 % by weight shown in the example of control is a very low concentration at which the compound is not used independently.

A synergistic effect can clearly be observed from Table 2, considering that each mixed preparation has a higher insecticidal activity than the added activity of each insecticidal components constituting the preparation, and also higher than the activity of each insecticidal component based on the same concentration of each component and total components of the preparation. The following Table 3 also shows the same tendency.

Table 2

The figures in parentheses indicate Compound Nos. of the present invention.

| Composition (Aerosols) | Knock-down ratio (%) 5' | 10' | 15' | Mortality (%) |
|---|---|---|---|---|
| [(1) 0.2 %] + [(4) .1%] | 47 | 75 | 100 | 78 |
| " + [(4),(±)-trans .1%] | 45 | 72 | 100 | 73 |
| " + [(6) .1%] | 34 | 68 | 100 | 100 |
| " + [(6),(±)-trans .1%] | 25 | 59 | 98 | 98 |
| " + [(6),(±)-cis,trans .1%] | 20 | 50 | 91 | 87 |
| " + [(12) .1%] | 27 | 42 | 93 | 85 |
| [(2) 0.2%] + [(6) .1%] | 31 | 63 | 99 | 98 |
| " + [(6),(±)-trans .1%] | 23 | 57 | 96 | 96 |
| " + [(6),(±)-cis,trans .1%] | 19 | 48 | 90 | 85 |
| " + [(12) .1%] | 25 | 39 | 87 | 80 |
| [(4) 0.1%] + [(1),(+)-trans .2%] | 40 | 63 | 100 | 72 |
| " + [(1),(±)-cis,trans .2%] | 28 | 56 | 95 | 52 |
| " + [(6) .1%] | 22 | 46 | 93 | 93 |
| " + [(6),(+)-trans .1%] | 28 | 65 | 100 | 100 |
| " + [(6),(±)-cis,trans .1%] | 20 | 45 | 90 | 81 |
| " + [(12) .1%] | 29 | 62 | 93 | 93 |
| [(6) 0.1%] + [(1),(±)-cis,trans .2%] | 21 | 49 | 88 | 88 |
| " + [(1),(+)-trans .2%] | 26 | 51 | 91 | 91 |

Table 2-continued

The figures in parentheses indicate Compound Nos. of the present invention.

| Composition (Aerosols) | | | Knock-down ratio (%) 5' | 10' | 15' | Mortality (%) |
|---|---|---|---|---|---|---|
| " | + [(4),(+)-trans | .2%] | 23 | 57 | 99 | 99 |
| " | + [(2),(+)-trans | .2%] | 22 | 50 | 86 | 85 |
| [(8) 0.2%] | + [(1) | .1%] | 44 | 68 | 100 | 62 |
| " | + [(1),(±)-cis,trans | .2%] | 35 | 61 | 92 | 60 |
| [(8) 0.2%] | + [(6) | .2%] | 30 | 56 | 92 | 92 |
| " | + [(12) | .1%] | 22 | 41 | 85 | 80 |
| [(12) 0.1%] | + [(1),(+)-trans | .1%] | 20 | 36 | 89 | 77 |
| " | + [(1),(±)-cis,trans | .2%] | 14 | 30 | 68 | 50 |
| " | + [(2),(+)-trans | .2%] | 16 | 32 | 84 | 70 |
| " | + [(4),(+)-trans | .2%] | 24 | 46 | 87 | 83 |
| | [(1) | .1%] | 15 | 29 | 58 | 16 |
| | [(1) | .2%] | 19 | 34 | 68 | 20 |
| | [(2) | .3%] | 14 | 28 | 50 | 15 |
| | [(2) | .2%] | 19 | 31 | 63 | 19 |
| | [(4) | .3%] | 13 | 29 | 52 | 16 |
| | [(4) | .1%] | 17 | 35 | 70 | 28 |
| | [(4) | .2%] | 20 | 43 | 82 | 39 |
| Control | [(6) | .3%] | 7 | 20 | 32 | 32 |
| (used in | [(6) | .1%] | 12 | 37 | 70 | 68 |
| the form of single | [(6) | .2%] | 18 | 53 | 81 | 81 |
| compound) | [(8) | .3%] | 12 | 22 | 49 | 20 |
| | [(8) | .2%] | 15 | 28 | 59 | 32 |
| | [(8) | .3%] | 19 | 33 | 67 | 48 |
| | [(12) | .4%] | 0 | 6 | 17 | 17 |
| | [(12) | .1%] | 3 | 15 | 35 | 31 |
| | [(12) | .2%] | 5 | 19 | 41 | 38 |
| | [(1),(+)-trans | .3%] | 12 | 20 | 49 | 13 |
| | [(1),(+)-trans | .2%] | 15 | 25 | 55 | 15 |
| | [(1),(±)-cis,trans | .3%] | 7 | 18 | 37 | 10 |
| | [(1),(±)-cis,trans | .2%] | 10 | 21 | 56 | 14 |
| | [(1),(±)-cis,trans | .3%] | 15 | 39 | 75 | 18 |
| | [(2),(+)-trans | .4%] | 10 | 21 | 43 | 12 |
| | [(2),(+)-trans | .2%] | 13 | 28 | 54 | 18 |
| | [(4),(+)-trans | 0.3-%] | 8 | 20 | 42 | 10 |
| | [(4),(+)-trans | .1%] | 12 | 30 | 61 | 24 |
| Control | [(4),(+)-trans | .2%] | 18 | 37 | 75 | 34 |
| (used in | [(6),(+)-trans | .3%] | 4 | 19 | 28 | 28 |
| the form of single | [(6),(+)-trans | .1%] | 7 | 36 | 59 | 57 |
| compound) | [(6),(+)-trans | .2%] | 10 | 47 | 76 | 75 |
| | [(6),(±)-cis,trans | .3%] | 2 | 9 | 19 | 19 |
| | [(6),(±)-cis,trans | .1%] | 4 | 19 | 47 | 44 |
| | [(6),(±)-cis,trans | .2%] | 7 | 26 | 60 | 58 |

Table 3

The figures in parentheses indicate Compound Nos. of the present invention.

| Composition (Aerosols) | | | Knock-down ratio (%) 5' | 10' | 15' | Mortality (%) |
|---|---|---|---|---|---|---|
| [(3) 0.2%] | + [(6) | .1%] | 34 | 65 | 100 | 100 |
| " | + [(12) | .1%] | 27 | 48 | 94 | 88 |
| [(5) 0.1%] | + [(12) | .1%] | 27 | 59 | 89 | 88 |
| [(7) 0.1%] | + [(1) | .2%] | 28 | 44 | 94 | 84 |
| " | + [(2) | .2%] | 27 | 42 | 90 | 78 |
| [(9) 0.2%] | + [(1) | .2%] | 40 | 64 | 100 | 60 |
| " | + [(2) | .2%] | 41 | 62 | 100 | 56 |
| " | + [(6) | .1%] | 28 | 53 | 90 | 90 |
| " | + [(12) | .1%] | 20 | 37 | 82 | 75 |
| [(1) 0.2%] | + [(1) | .2%] | 45 | 76 | 100 | 72 |
| " | + [(2) | .2%] | 43 | 72 | 100 | 70 |
| " | + [(6) | .1%] | 35 | 69 | 100 | 100 |
| " | + [(12) | .1%] | 33 | 54 | 98 | 98 |
| " | + [(6),(±)-cis,trans | .1%] | 27 | 53 | 99 | 99 |
| [(11) 0.1%] | + [(2) | .1%] | 19 | 42 | 85 | 60 |
| | [(3) | .2%] | 17 | 32 | 53 | 18 |
| | [(5) | .2%] | 15 | 29 | 50 | 15 |
| Control | [(7) | .1%] | 1 | 8 | 19 | 18 |
| (used in | [(9) | .1%] | 10 | 21 | 46 | 19 |
| the form of single | [(10) | .2%] | 15 | 30 | 64 | 27 |
| compound) | [(11) | .1%] | 0 | 5 | 15 | 15 |
| | [(1) | .2%] | 15 | 29 | 58 | 16 |
| Control | [(2) | .2%] | 14 | 28 | 50 | 15 |
| (used in | [(6) | .1%] | 7 | 20 | 32 | 32 |
| the form of single | [(6),(±)-cis,trans | .1%] | 2 | 9 | 19 | 19 |
| compound) | [(12) | .1%] | 0 | 6 | 17 | 17 |

TEST EXAMPLE 3

In the same manner as in Test example 2, in order to investigate the synergistic action between (+)-cis,trans-(for example 2:8)-chrysanthemates themselves, and between said chrysanthemates and the different type chrysanthemates according to the present invention, the two chrysanthemates were formulated into mosquito coils shown in the following Table 4.

0.8 Gram of each mosquito coil was burnt in a (6 ft)³ Peet Grady's Chamber which was used for the aerosol test in Test example 2. Thereafter, 50 northern house mosquito adults (*Culex pipens pullens*) per group were liberated in the smoke, and the number of knocked down adults with lapse of time was counted. The values of $KT_{50}$ (a period required for 50% knock-down), the periods required for 80% knock-down, and the durations of activity are summarized in Table 4 and Table 5.

A concentration of 0.1 % shown in the example of control is a very low concentration at which a compound is not used independently.

From Table 4, the same synergistic effect as in aerosols can be observed. The following Table 5 shows the same tendency.

As clearly shown in the results of Test example 2 (Tables 2 and 3) and Test example 3 (Tables 4 and 5), each mixed preparation shows a remarkable synergistic effect due to mixing, compared with an activity of respective insecticidal component constituting the preparation.

Table 4

| The figures in parentheses indicate Compound Nos. of the present invention. | | | | | |
|---|---|---|---|---|---|
| | Composition (mosquito coil) | | $KT_{50}$ (min) | 80% Knock-down ratio | |
| | | | | Time required (min) | Duration (min) |
| | [(2) 0.2%] + [(6) | 0.1%] | 8 | 29 | >91 |
| | " + [(6),(+)-trans | 0.1%] | 8.4 | 33 | >87 |
| | " + [(6),(±)-cis,trans | 0.1%] | 13 | 53.4 | >66.6 |
| | " + [(12) | 0.05%] | 10.4 | 53 | >67 |
| | " + [(12) | 0.1%] | 8.5 | 32.4 | >87.6 |
| | " + [(12) | 0.2%] | 6.2 | 26.1 | >93.9 |
| | " + [(12),(+)-trans | 0.1%] | 9.1 | 40.2 | >79.8 |
| | " + [(12),(±)-cis,trans | 0.2%] | 8.8 | 35.2 | >84.8 |
| | [(4) 0.2%] + [(8) | 0.1%] | 4.8 | 26 | >94 |
| | " + [(12) | 0.1%] | 4 | 17 | >103 |
| | [(6) 0.1%] + [(2),(+)-trans | 0.2%] | 8 | 30 | >90 |
| | " + [(2),(±)-cis,trans | 0.3%] | 10.2 | 50 | >70 |
| | [(8) 0.1%] + [(4),(+)-trans | 0.1%] | 6 | 32 | >88 |
| | [(12) 0.1%] + [(2),(+)-trans | 0.2%] | 8.9 | 36.5 | >83.5 |
| | " + [(2),(±)-cis,trans | 0.3%] | 9.5 | 46 | >74 |
| Control (used in the form of single compound) | [(2) | 0.2%] | 21 | >120 | — |
| | [(2) | 0.25%] | 15.2 | >120 | — |
| | [(2) | 0.3%] | 9.3 | 80 | >40 |
| | [(2) | 0.4%] | 8 | 29 | >91 |
| | [(4) | 0.2%] | 8.7 | 32 | >88 |
| | [(4) | 0.3%] | 6.2 | 28 | >92 |
| | [(6) | 0.1%] | 90 | >120 | — |
| | [(6) | 0.3%] | 30 | 40 | >80 |
| | [(6) | 0.4%] | 22 | 35 | >85 |
| | [(8) | 0.1%] | >120 | >120 | — |
| | [(8) | 0.3%] | 11.5 | 85 | >35 |
| | [(12) | 0.05%] | >120 | >120 | — |
| | [(12) | 0.1%] | 72 | >120 | — |
| | [(12) | 0.2%] | 43 | 70 | >50 |
| | [(12) | 0.25%] | 40 | 61 | >59 |
| Control (used in the form of single compound) | [(12) | 0.3%] | 35.5 | 50 | >70 |
| | [(12) | 0.4%] | 30.2 | 42 | >78 |
| | [(2),(+)-trans | 0.2%] | 25.4 | >120 | — |
| | [(2),(+)-trans | 0.3%] | 11.5 | 85.5 | >34.5 |
| | [(2),(+)-cis,trans | 0.3%] | >120 | >120 | — |
| | [(2),(±)-cis,trans | 0.4%] | 29.5 | >120 | — |
| | [(4),(+)-trans | 0.1%] | 26 | >120 | — |
| | [(4),(+)-trans | 0.2%] | 9.2 | 40 | >80 |
| | [(6),(+)-trans | 0.1%] | 194 | >120 | — |
| | [(6),(+)-trans | 0.3%] | 41 | 68 | >52 |
| | [(6),(±)-cis,trans | 0.1%] | >120 | >120 | — |
| | [(6),(±)-cis,trans | 0.3%] | 71 | 110 | >10 |
| | [(12),(+)-trans | 0.1%] | 82 | >120 | — |
| | [(12),(+)-trans | 0.3%] | 49 | 78 | >42 |
| | [(12),(±)-cis,trans | 0.2%] | 79 | >120 | — |
| | [(12),(±)-cis,trans | 0.4%] | 57 | 85 | >35 |

Table 5

| The figures in parentheses indicate Compound Nos. of the present invention. | | | | | |
|---|---|---|---|---|---|
| | Composition (mosquito coil) | | $KT_{50}$ (min) | 80% Knock-down ratio | |
| | | | | Time required (min) | Duration (min) |
| | [(3) 0.2%] + [(6) | 0.1%] | 8.2 | 28 | >92 |
| | " + [(6),(+)-trans | 0.1%] | 8.6 | 35 | >85 |
| | " + [(6),(±)-cis,trans | 0.1%] | 12.8 | 151.3 | >68.7 |
| | " + [(12) | 0.1%] | 8 | 25 | >95 |

Table 5-continued

The figures in parentheses indicate Compound Nos. of the present invention.

| Composition (mosquito coil) | | KT$_{50}$ (min) | 80% Knock-down ratio Time required (min) | Duration (min) |
|---|---|---|---|---|
| [(8) 0.2%] + [(6) | 0.1%] | 7.7 | 28 | >92 |
| " + [(6),(+)-trans | 0.1%] | 8.5 | 39 | >81 |
| " + [(6),(±)-cis,trans | 0.1%] | 9. | 47.9 | >72.1 |
| " + [(121) | 0.1%] | 7.5 | 25 | >95 |
| " + [(12),(+)-trans | 0.1%] | 7.9 | 30.2 | >89.8 |
| [(9) 0.2%] + [(6) | 0.1%] | 8 | 3.13 | >88.7 |
| " + [(6),(+)-trans | 0.1%] | 8.6 | 33.5 | >86.5 |
| " + [(6),(±)-cis,trans | 0.1%] | 9.3 | 46 | >74 |
| " + [(12) | 0.1%] | 7.7 | 29.3 | >90.7 |
| [(6) 0.1%] + (4),(+)-trans | 0.2%] | 8.5 | 34.5 | >85.5 |
| " + [(3),(±)-cis,trans | 0.3%] | 10.5 | 37 | >83.3 |
| " + [(8),(+)-trans | 0.2%] | 8 | 29.7 | >90.3 |
| " + [(8),(±)-cis,trans | 0.3%] | 9.2 | 34.1 | >85.9 |
| " + [(9),(+)-trans | 0.2%] | 8.8 | 32.8 | >87.2 |
| " +[(9),(±)-cis,trans | 0.3% | 8.2 | 31.4 | >88.6 |
| [(12) 0.1%] + [(3),(+)-trans | 0.2%] | 8.3 | 31.7 | >88.3 |
| " + [(3),(±)-cis,trans | 0.3% | 10.2 | 36.6 | >83.4 |
| " + [(8),(+)-trans | 0.2%] | 7.8 | 27.4 | >92.6 |
| [(12) 0.1%] + [(8),(±)-cis,trans | 0.3%] | 8.9 | 30.3 | >88.7 |
| " + [(9),(+)-trans | 0.2%] | 7.9 | 30.6 | >89.4 |
| " +[(9),(±)-cis,trans | 0.3%] | 8.1 | 32.3 | >87.7 |
| [(3) | 0.2%] | 21 | >120 | — |
| [(8) | 0.2%] | 12.2 | 85 | >35 |
| [(9) | 0.2%] | 15 | >120 | — |
| [(6) | 0.15] | 90 | >120 | — |
| [(12) | 0.1%] | 72 | >120 | — |
| [(3),(+)-trans | 0.2%] | 24.7 | >120 | — |
| [(3),(±)-cis,trans | 0.3%] | >120 | >120 | — |
| Control [(6),(+)-trans | 0.1%] | 94 | >120 | — |
| [(6),(±)-cis,trans | 0.1%] | >120 | >120 | — |
| [(8),(+)-trans | 0.2%] | 14.8 | >120 | — |
| [(8),(±)-cis,trans | 0.3%] | 50.7 | >120 | — |
| [(9),(+)-trans | 0.2%] | 18.2 | >120 | — |
| [(9),(±)-cis,trans | 0.3%] | 58.5 | >120 | — |
| [(12),(+)-trans | 0.1%] | 82 | >120 | — |

In the preparation of insecticidal compositions of the present invention, the present compounds may be formulated, like pyrethoids, into any desired form of oil spray, emulsifiable concentrates, dusts, aerosols, wettable powder, granules, mosquito coil, heating or non-heating fumigant, bait and luring dust or solid preparation, by methods well known to those skilled in the art, using auxiliary agents and/or carriers for common insecticidal compositions.

Furthermore, the present compounds may be increased in their insecticidal activity when used in combination with a known synergist for pyrethroid such as α-[2-(2-butoxyethoxy)-ethoxy]-4,5-methylenedioxy-2-propyltoluene (referred to as "piperonylbutoxide"), 1,2-methylenedioxy-4-[2-(octylsulfinyl)propyl]-benzene (referred to as "sulfoxide"), 4-(3,4-methylenedioxy-phenyl)-5-methyl-1,3-dioxane (referred to as "safroxane"), N-(2-ethylhexyl)bicyclo[2,2,1]hepta-5-ene-2,3-dicarboximide (referred to as "MGK-264"), octachlorodipropylether (referred to as "S-421"), or isobornylthiocyanoacetate (referred to as "Thanite"), and with a known synergist for allethrin or pyrethrin.

Although the chrysanthemate type compounds are generally a little inferior in the resistance to light, heat and oxidation, the compounds can be formulated into insecticidal compositions having a more stable activity by incorporating, as a stabilizing agent, a proper amount of antioxidants, or U.V. absorbers such as phenol derivatives including BHT and BHA, bisphenol derivatives, arylamine derivatives including phenyl-α-naphthylamine, phenyl-β-naphthylamine and condensation products resulting from phenetidine and acetone, or benzophenone compounds.

In addition, the present compounds may be formulated into multi-purpose compositions of high activity by incorporating other active ingredients such as organochlorine type insecticides, e.g., DDT, BHC, and methoxychlor; organophosphorus type insecticides, e.g., 0,0-dimethyl-0-(3-methyl-4-nitrophenyl)-phosphorothioate (referred to as "Sumithion", registered trade name of Sumitomo Chemical Co., Ltd.), and 0,0-dimethyl-0-(2,2-dichlorovinyl)phosphate (referred to as "DDVP"); carbamate type insecticides, e.g., 1-naphthyl-N-methylcarbamate, 3,4-dimethylphenyl-N-methylcarbamate, and 3,5-dimethylphenyl-N-methylcarbamate; other insecticides; microbial insecticides, e.g., B.T. and B.M. fungicides; nematocides; acaricides; herbicides; fertilizer; insect hormone compounds; or other agricultural chemicals. Furthermore, a synergistic effect can also be expected in combination of the compositions.

The preparation and activity of the compositions of the present invention will be illustrated with reference to the following preparation and examples, which are only given for the purpose of illustration, and not to be interpreted as limiting.

Preparation 1

To 0.05 part of each of the compounds (1), (2), (3), (4), (7), (8), (9), (10) and (11) was added 0.1 part of the compound (6). The mixtures were each dissolved in kerosene to 100 parts of total weight. Ten oil sprays were thus obtained.

Preparation 2

To 0.1 part of each of the compounds from (1) to (10) was added 0.1 part of the compound (12). The mixtures were each dissolved in kerosene to 100 parts of total weight. Ten oil sprays were thus obtained.

Preparation 3

To 10 parts of each of the compounds (4), (5), (6), (10), (11) and (12) were added 5 parts of the compound (2), 30 parts of safroxane, 10 parts of Sorpol SM-200 (registered trade name for an emulsifier sold by Toho Kagaku Co., Ltd.) and 45 parts of xylene. The mixtures were each thoroughly mixed to make a solution. Six emulsifiable concentrates were thus obtained.

Preparation 4

To 20 parts of each of the compounds (1), (2), (6) and (12) were added 5 parts of 5-propargyl-2-methyl-3-furylmethyl-($\pm$)-cis,trans-chrysanthemate, 5 parts of Sorpol SM-200 (the same as above) and 70 parts of 300 mesh talc. The mixtures were each thoroughly mixed by means of a mortar. Four wettable powders were thus obtained.

Preparation 5

To 1 part of each of the compounds (1), (2), (6) and (12) were added 1 part of 5-propargyl-$\alpha$-ethynyl-furfuryl-($\pm$)-cis,trans-chrysanthemate and 2 parts of piperonyl-butoxide. The mixtures were each dissolved in 20 parts of acetone, and 96 parts of 300 mesh diatomaceous earth were added thereto. The resulting mixtures were each thoroughly mixed by means of a mortar, and then acetone was removed by evaporation. Four dusts were thus obtained.

Preparation 6

0.1 Gram of each of the compounds (5), (6), (7), (8), (9), (10) and (12), 0.3 g of the compound (2) and 0.2 g of BHT were dissolved in 20 ml. of methanol. The solution were each uniformly mixed with 99.4 g of a mosquito coil carrier containing Tabu powder, Pyrethrum marc and wood powder in a ratio of 3 : 5 : 1, and then methanol was evaporated. Each residue was given 150 ml of water, kneaded thoroughly, shaped into a mosquito coil and dried. Seven mosquito coils were thus obtained.

Preparation 7

0.2 Gram of each of the compounds (2), (4), (6), (9) and (13), 0.2 g of BHT and 0.2 g of 5-propargylfurfuryl-($\pm$)-cis,trans-chrysanthemate were dissolved in 20 ml of methanol. The solutions were each treated in the same way as described in Preparation 6 to give a mosquito coil.

Preparation 8

0.1 Gram of each of the compounds (2), (3), (4), (8) and (9), 0.05 g of the compound (12), 0.1 g of BHT and 0.1 g of piperonyl-butoxide were dissolved in a proper amount of chloroform. The solutions were each adsorbed uniformly to the surface of an asbestos piece of 3.5 cm $\times$ 1.5 cm in area and 0.3 mm in thickness, and then another piece of asbestos of the same size was sticked to the surface. Five fibrous heating fumigant insecticidal compositions for use on a heater were thus obtained. Pulp plate may be used in place of asbestos as a fibrous carrier having the same effect.

Preparation 9

0.05 Gram of each of the compounds (1), (2), (4), (6), (11) and (12), 0.05 g of 5-propargyl-2-methyl-3-furylmethyl-($\pm$)-cis,trans-chrysanthemate, 0.2 g of BHT, and 0.05 g of piperonyl-butoxide were dissolved in a proper amount of chloroform. The solutions were each treated in the same manner as described in Preparation 8 to give a fibrous heating fumigant insecticidal composition for use on a heater.

Preparation 10

0.2 Part of the compound (1), 0.1 part of the compound (12), and 0.1 part of 5-propargyl-$\alpha$-ethynylfurfuryl-(+)-trans-chrysanthemate were dissolved in a mixture of 7 parts of xylene and 7.6 parts of deodorized kerosene. The solution was filled in an aerosol container. After attaching a valve portion to the container, 85 parts of propellant (e.g. liquefied petroleum gas) were charged therein under pressure through the valve. An aerosol was thus obtained.

Preparation 11

0.2 Part of the compound (2), 0.2 part of 3-phenoxybenzyl-($\pm$)-cis,trans-chrysanthemate, and 0.4 part of piperonyl-butoxide were dissolved in a mixture of 7 parts of xylene and 7.2 parts of deodorized kerosene. The solution was treated in the same manner as described in Preparation 10 to give an aerosol.

Preparation 12

0.2 Part of the compound (1), 0.5 part of a pyrethrin extract containing 20 % of pyrethrin, and 0.1 part of 3-phenoxybenzyl-(+)-trans-chrysanthemate were dissolved in a mixture of 7 parts of xylene and 7.2 parts of deodorized kerosene. The solution was treated in the same manner as described in Preparation 10 to give an aerosol.

Preparation 13

0.2 Part of the compound (1), 0.05 part of the compound (2), and 0.5 part of Sumithion were dissolved in a mixture of 7 parts of xylene and 7.25 parts of deodorized kerosene. The solution was treated in the same manner as described in Preparation 10 to give an aerosol.

Preparation 14

3 Parts of the compound (6), 1 part of the compound (9), 1 part of 3,4-dimethylphenyl-N-methyl-carbamate, 5 parts of Toyolignin CT (registered trade name of Toyo Spinning Co., Ltd.) and 90 parts of GSM clay (registered trade name for clay sold by Zieklite Mining Co. Ltd.) were thoroughly mixed by means of a mortar. Then, the mixture was well mixed with 10 % by its weight of water, granulated by means of a granulator and air-dried to give a granular preparation.

The insecticidal activity of the present compositions thus obtained was as follows.

EXAMPLE 9

5 Milliliters of each of the oil sprays formulated according to Preparation 1 were sprayed, using Campbel's turn table method (the same as above). About 100 house-fly adults (Musca domestica) per group were exposed to the descending mist for 10 minutes. By the next day, more than 80 of the flies were killed with any oil spray.

EXAMPLE 10

About 50 northern house mosquito adults (*Culex pipens pullens*) were liberated in a (70 cm)$^3$ glass chamber. 0.7 Milliliter of each of the oil sprays formulated according to Preparation 2 was sprayed under a pressure of 20 lb/in² through a glass atomizer. Then, more than 80 % of the adults were knocked down within 10 minutes. By the next day, more than 80 % of the mosquitoes were killed with any oil spray.

EXAMPLE 11

The emulsifiable concentrates formulated according to Preparation 3 were each diluted 50,000 times with water. 2 Liters of each test emulsion so prepared were taken in a styrene case of 23 cm × 30 cm in area and 6 cm in depth, and about 100 full grown larvae of northern house mosquito (Culex pipens pullens) were liberated therein. By the next day, more than 90 % of the larvae were killed with any concentrate.

EXAMPLE 12

About 50 northern house mosquito adults (Culex pipens pullens) were liberated in a (70 cm)³ glass chamber in which a battery-type small fan (wing diameter 13 cm) was set and run. 0.1 Gram of each of the mosquito coils formulated according to Preparations 6 and 7 was ignited at both ends and placed in the chamber. More than 80 % of the adults were knocked down within 20 minutes with any mosquito coil. By the next day, more than 80 % of the adults were killed.

EXAMPLE 13

About 50 house-fly adults (Musca domestica) were liberated in a (70 cm)³ glass chamber in which a battery-type small fan (wing diameter 13 cm) was set and run. Each of heating fumigant compositions formulated according to Preparations 8 and 9 was placed on a heater in the chamber and heated. More than 80 % of the adults were knocked down within 20 minutes with any fumigant.

EXAMPLE 14

The insecticidal activity on house-fly adults (Musca domestica) of the aerosols formulated according to Preparation 10, 11, 12 and 13 was tested by the aerosol test method (the same as above) using a (6 ft)³ Peet Grady's chamber. The results are as shown in Table 6.

Table 6

| Composition | | Knock-down ratio (%) | | | Mortality (%) |
|---|---|---|---|---|---|
| | | 5 min. | 10 min. | 15 min. | |
| Aerosol | (Preparation 10) | 39 | 60 | 100 | 100 |
| " | ( " 11) | 27 | 54 | 97 | 97 |
| " | ( " 12) | 38 | 67 | 98 | 85 |
| " | ( " 13) | 35 | 69 | 100 | 100 |

EXAMPLE 15

A glass Petri dish of 14 cm in inside diameter was coated on the inside wall with butter, leaving at the lower part an uncoated portion of 1 cm in width. Onto the bottom of the dish, each of the dusts formulated according to Preparation 5 was uniformly dusted in a proportion of 2 g/cm².

Subsequently, 10 German cockroach adults (Blattella germanica) per group were liberated in the dish and allowed to come into contact with the dust for 30 minutes. After three days, more than 70 % of the knocked down adults were killed.

EXAMPLE 16

In 1/50,000 Wagner pots were grown rice plants which had elapsed 45 days after sowing. The wettable powders formulated according to Preparation 4 were each diluted 500 times with water. Each test solution so prepared was individually sprayed on the rice plants in a proportion of 10 ml per pot. Each pot was covered with wire net and about 30 adults of green rice leafhoppers (Nephotettix cincpiceps) were liberated in the pot. After 1 day, more than 80 % of the hoppers were killed.

EXAMPLE 17

Each of the emulsifiable concentrates formulated according to Preparation 3 was diluted 100 times with water. About 10 third to fourth instar larvae of the tobacco cut worm (Spodoptera litura) were liberated in a glass Petri dish of 14 cm in inside diameter and 1 ml of each of dilute solutions were sprayed. Thereafter, the larvae were fed and allowed to stand in another dish, and after two days more than 90 % of the larvae were killed with any concentrate.

EXAMPLE 18

10 Liters of water were taken in a 14-l polypropylene bucket, and 1 g of each of the granular preparations formulated according to Preparation 14 was added thereto. After one day, about 100 full grown northern house mosquito larvae (Culex pipens pullens) were liberated in the water. More than 90 % of the larvae were killed within 24 hours.

What we claim is:

1. An insecticidal composition for use against mosquitoes, flies, cockroaches, leafhoppers and cut worms containing as an active ingredient an insecticidally effective amount of (+)-cis, transchrysanthemate of the formula,

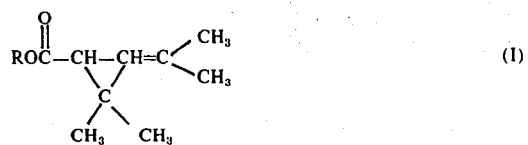

wherein R is a member selected from the group consisting of the radicals,

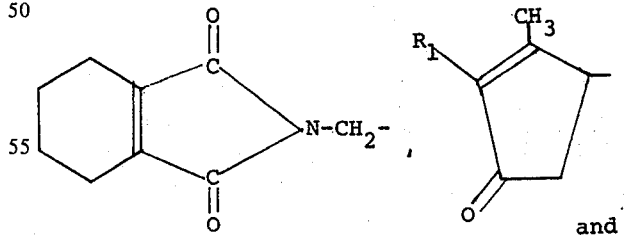

and

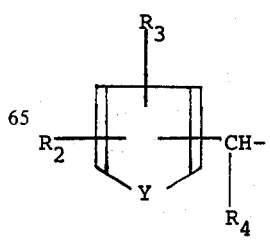

in which $R_1$ is allyl or propargyl, $R_2$ is propargyl, benzyl or phenoxy, $R_3$ is hydrogen or methyl, $R_4$ is hydrogen or ethynyl, and Y is —CH=CH— or oxygen, and an inert carrier, said (+)-cis, trans-chrysanthemate containing 10 to 30% by weight of (+)-cis-chrysanthemate and 70 to 90% by weight of (+)-trans-chrysanthemate.

2. The insecticidal composition according to claim 1, wherein said composition contains 0.05 to 90 % by weight of the active ingredient.

3. The insecticidal composition according to claim 1, wherein said (+)-cis,trans-chrysanthemate of the formula (I) consists of 20 % by weight of (+)-cis-form and 80 % by weight of (+)-trans-form.

4. The insecticidal composition according to claim 1, wherein said (+)-cis,trans-chrysanthemate is a compound of the formula,

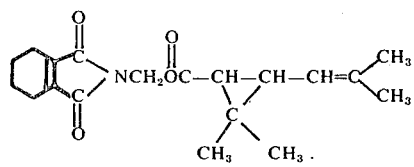

5. The insecticidal composition according to claim 1, wherein said (+)-cis,trans-chrysanthemate is a compound of the formula,

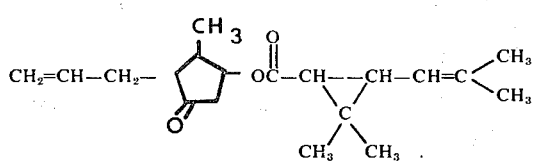

6. The insecticidal composition according to claim 1, wherein said (+)-cis,trans-chrysanthemate is (±) or (+)-2-allyl-3-methyl-cyclopent-2-ene-1-one-4-yl-(+)-cis,trans-chrysanthemate.

7. The insecticidal composition according to claim 1, wherein said (+)-cis,trans-chrysanthemate is a compound of the formula,

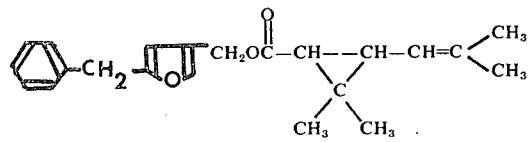

8. The insecticidal composition according to claim 1, wherein said (+)-cis,trans-chrysanthemate is a compound of the formula,

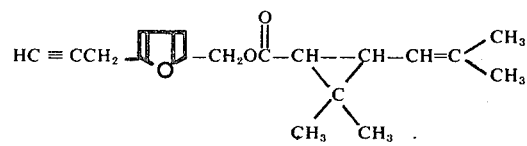

9. The insecticidal composition according to claim 1, wherein said (+)-cis,trans-chrysanthemate is a compound of the formula,

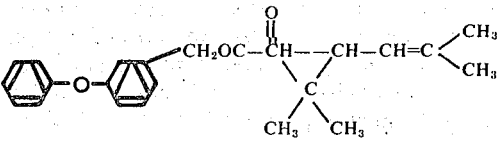

10. An insecticidal composition for use against mosquitoes, flies, cockroaches, leafhoppers and cut worms containing an inert carrier and as active ingredients an insecticidally effective amount of (a) one of (+)-cis, transchrysanthemates as claimed in claim 1, and (b) one chrysanthemate of the general formula (I) having in the acid moiety an isomer ratio different from that in (a) and whose alcohol moiety which is as defined as R in general formula I is different in structure from the alcohol moiety in (a).

11. The insecticidal composition according to claim 10, wherein the ratio of (a) to (b) is from 10 : 2 to 10 : 50.

12. The insecticidal composition according to claim 10, wherein said composition contains 0.2 to 90 % by weight of the active ingredient.

13. The insecticidal composition according to claim 10, wherein the (+)-cis,trans-chrysanthemate of (a) is a compound of the formula,

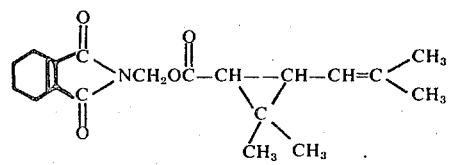

14. The insecticidal composition according to claim 10, wherein the (+)-cis,trans-chrysanthemate of (a) is a compound of the formula,

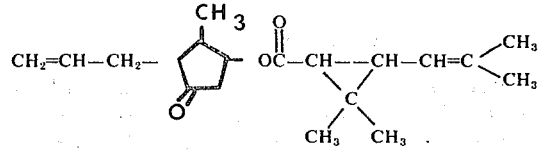

15. The insecticidal composition according to claim 10, wherein the (+)-cis,trans-chrysanthemate of (a) is (±) or (+)-2-allyl-3-methyl-cyclopent-2-ene-1-one-4-yl-(+)-cis,trans-chrysanthemate.

16. The insecticidal composition according to claim 10, wherein the (+)-cis,trans-chrysanthemate of (a) is a compound of the formula,

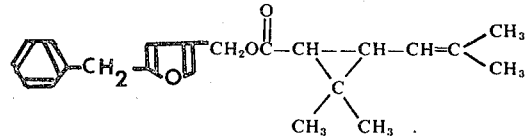

17. The insecticidal composition according to claim 10, wherein the (+)-cis,trans-chrysanthemate of (a) is a compound of the formula,

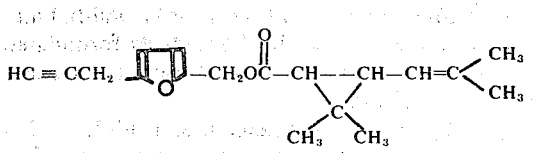

18. The insecticidal composition according to claim 10, wherein the (+)-cis,trans-chrysanthemate of (a) is a compound of the formula,

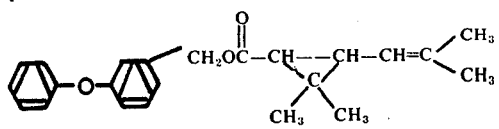

19. A method for killing insects selected from the group consisting of mosquitoes, flies, cockroaches, leafhoppers and cut worms, which comprises contacting said insects with an insecticidal composition according to claim 1 containing 0.05 – 90% by weight of the active ingredient.

* * * * *